(12) United States Patent
Buch-Rasmussen et al.

(10) Patent No.: US 8,084,053 B2
(45) Date of Patent: Dec. 27, 2011

(54) DRY MOULDABLE DRUG FORMULATION

(75) Inventors: Thomas Buch-Rasmussen, Gentofte (DK); James M. Flink, Klampenborg (DK); Jens Ulrich Poulsen, Virum (DK); Søren Aasmul, Holte (DK); Philip Hansen, Holte (DK); Claus Juul Mortensen, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/462,794

(22) Filed: Aug. 7, 2009

(65) Prior Publication Data

US 2010/0196477 A1 Aug. 5, 2010

Related U.S. Application Data

(63) Continuation of application No. 11/052,645, filed on Feb. 7, 2005, now Pat. No. 7,666,844, which is a continuation of application No. 09/550,857, filed on Apr. 17, 2000, now abandoned.

(60) Provisional application No. 60/139,403, filed on Jun. 14, 1999.

(30) Foreign Application Priority Data

Apr. 16, 1999 (DK) ................................. 1999 00514

(51) Int. Cl.
*A61F 2/00* (2006.01)
*A61K 9/22* (2006.01)
*C07H 1/00* (2006.01)

(52) U.S. Cl. ...... 424/423; 514/23; 536/1.11; 536/123.1; 604/60; 604/809.1

(58) Field of Classification Search .................... 604/60, 604/809.1; 536/1.11, 123.1; 424/423; 514/23
See application file for complete search history.

(56) References Cited

U.S. PATENT DOCUMENTS

| | | | |
|---|---|---|---|
| 3,948,263 A | 4/1976 | Drake et al. | |
| 4,015,033 A | 3/1977 | Nield | |
| 4,089,334 A | 5/1978 | Schwebel et al. | |
| 4,153,406 A | 5/1979 | Dittmann et al. | |
| 4,576,604 A | 3/1986 | Guittard et al. | |
| 4,671,953 A | 6/1987 | Stanley et al. | |
| 4,697,575 A | 10/1987 | Horowitz | |
| 4,920,727 A | 5/1990 | Ristamaki et al. | |
| 4,962,091 A | 10/1990 | Eppstein et al. | |
| 5,153,002 A | 10/1992 | McMullen et al. | |
| 5,356,635 A | 10/1994 | Raman et al. | |
| 5,372,590 A | 12/1994 | Haber et al. | |
| 5,403,595 A | 4/1995 | Kitchell et al. | |
| 5,429,822 A | 7/1995 | Gresser et al. | |
| 5,434,146 A | 7/1995 | Labrie et al. | |
| 5,486,362 A | 1/1996 | Kitchell et al. | |
| 5,525,352 A | 6/1996 | Kontos et al. | |
| 5,536,503 A | 7/1996 | Kitchell et al. | |
| 5,541,172 A | 7/1996 | Labrie et al. | |
| 5,542,920 A | 8/1996 | Cherif-Cheikh | |
| 5,543,156 A | 8/1996 | Roorda et al. | |
| 5,567,439 A | 10/1996 | Myers et al. | |
| 5,582,591 A | 12/1996 | Cheikh | |
| 5,595,760 A | 1/1997 | Cherif-Cheikh | |
| 5,616,123 A | 4/1997 | Cheikh | |
| 5,629,303 A | 5/1997 | Labrie et al. | |
| 5,633,000 A | 5/1997 | Grossman et al. | |
| 5,656,298 A | 8/1997 | Kitchell et al. | |
| 5,660,846 A | 8/1997 | Cheikh | |
| 5,695,463 A | 12/1997 | Cherif-Cheikh | |
| 5,716,981 A | 2/1998 | Hunter et al. | |
| 5,762,961 A | 6/1998 | Roser et al. | |
| 5,766,637 A | 6/1998 | Shine et al. | |
| 5,776,107 A | 7/1998 | Cherif-Cheikh | |
| 5,783,567 A | 7/1998 | Hedley et al. | |
| 5,814,340 A | 9/1998 | Labrie et al. | |
| 5,817,343 A | 10/1998 | Burke | |
| 5,823,994 A | 10/1998 | Sharkey et al. | |
| 5,833,891 A | 11/1998 | Subramaniam et al. | |
| 5,837,276 A | 11/1998 | Cheikh | |
| 5,851,547 A | 12/1998 | Fujioka et al. | |
| 5,858,388 A | 1/1999 | Grossman et al. | |
| 5,861,387 A | 1/1999 | Labrie et al. | |
| 5,874,029 A | 2/1999 | Subramaniam et al. | |
| 5,882,682 A | 3/1999 | Rork et al. | |
| 5,886,026 A | 3/1999 | Hunter et al. | |
| 5,929,196 A | 7/1999 | Kissel et al. | |
| 5,945,128 A | 8/1999 | Deghenghi | |
| 5,980,948 A | 11/1999 | Goedemoed et al. | |
| 5,994,341 A | 11/1999 | Hunter et al. | |
| 6,004,573 A | 12/1999 | Rathi et al. | |
| 6,077,523 A | 6/2000 | Deghenghi | |

(Continued)

FOREIGN PATENT DOCUMENTS

CA 1 196 864 11/1985

(Continued)

OTHER PUBLICATIONS

Yamakawa, "Sustained Release of Insulin by Double Layered Implant using poly(D,L lactic acid)," J. Pharm Sciences, vol. 79, No. 6, pp. 505-509, Jun. 1990.
Office Action dated Feb. 25, 2008 in U.S. Appl. No. 10/341,142 by Buch-Rasmussen et al., filed Jan. 13, 2003.
Office Action dated May 8, 2008 in U.S. Appl. No. 10/322,143 by Hansen et al., filed Dec. 18, 2002.
Office Action dated Sep. 5, 2008 inU.S. Appl. No. 10/341,142 by Buch-Rasmussen et al., filed Jan. 13, 2003.
Response submitted Sep. 9, 2008 in U.S. Appl. No. 10/322,143 by Hansen et al.
Office Action dated Sep. 29, 2008 in U.S. Appl. No. 10/322,143 by Hansen e al., filed Dec. 18, 2002.
Response submitted Feb. 5, 2009 in U.S. Appl. No. 10/341,142 by Buch-Rasmussen et al.

(Continued)

Primary Examiner — Paul V. Ward
(74) Attorney, Agent, or Firm — Wesley A. Nicolas; Marc A. Began

(57) ABSTRACT

Solid pharmaceutical compositions and methods of making and administering for parenteral injection comprising a binder and at least one therapeutic agent. The pharmaceutical composition has the strength to be injected directly with the need of using cannulas or the like.

17 Claims, 4 Drawing Sheets
(2 of 4 Drawing Sheet(s) Filed in Color)

U.S. PATENT DOCUMENTS

| | | | |
|---|---|---|---|
| 6,098,675 | A | 8/2000 | Runft |
| 6,117,949 | A | 9/2000 | Rathi et al. |
| 6,126,956 | A | 10/2000 | Grossman et al. |
| 6,139,574 | A | 10/2000 | Vacanti et al. |
| 6,143,037 | A | 11/2000 | Goldstein et al. |
| 6,149,864 | A | 11/2000 | Dillow et al. |
| 6,159,490 | A | 12/2000 | Deghenghi |
| 6,176,874 | B1 | 1/2001 | Vacanti et al. |
| 6,183,781 | B1 | 2/2001 | Burke |
| 6,193,994 | B1 | 2/2001 | Lee et al. |
| 6,197,575 | B1 | 3/2001 | Griffith et al. |
| 6,201,072 | B1 | 3/2001 | Rathi et al. |
| 6,224,630 | B1 | 5/2001 | Bao et al. |
| 6,224,794 | B1 | 5/2001 | Amsden et al. |
| 6,231,904 | B1 | 5/2001 | Mueller |
| 6,232,340 | B1 | 5/2001 | Zhang et al. |
| 6,241,771 | B1 | 6/2001 | Gresser et al. |
| 6,290,991 | B1 | 9/2001 | Roser et al. |
| 6,485,453 | B1 | 11/2002 | Buch-Rasmussen |
| 2002/0111603 | A1 | 8/2002 | Cherif-Cheikh |
| 2003/0054044 | A1 | 3/2003 | Potter et al. |
| 2003/0161881 | A1 | 8/2003 | Hansen et al. |
| 2003/0234466 | A1 | 12/2003 | Buch-Rasmussen |
| 2005/0202072 | A1 | 9/2005 | Buch-Rasmussen et al. |

FOREIGN PATENT DOCUMENTS

| | | |
|---|---|---|
| EP | 0 049 068 | 12/1985 |
| EP | 0 838 209 | 4/2000 |
| EP | 1 092 433 | 4/2001 |
| GB | 2 091 554 | 4/1982 |
| JP | 59167513 | 9/1984 |
| JP | 5255071 | 10/1993 |
| JP | 11508224 | 7/1999 |
| WO | 92/02211 | 2/1992 |
| WO | WO 92/02211 | 2/1992 |
| WO | WO 93/10758 | 6/1993 |
| WO | WO 93/17662 | 9/1993 |
| WO | WO 93/23110 | 11/1993 |
| WO | WO 94/22423 | 10/1994 |
| WO | WO 94/24263 | 10/1994 |
| WO | WO 96/03978 | 2/1996 |
| WO | 96/07397 | 3/1996 |
| WO | 96/07398 | 3/1996 |
| WO | 96/07440 | 3/1996 |
| WO | WO 96/07397 | 3/1996 |
| WO | WO 96/07398 | 3/1996 |
| WO | WO 96/07440 | 3/1996 |
| WO | WO 96/08289 | 3/1996 |
| WO | WO 98/32427 | 7/1998 |
| WO | WO 99/33853 | 7/1999 |
| WO | WO 00/32071 | 6/2000 |
| WO | WO 00/53160 | 9/2000 |
| WO | WO 00/62759 | 10/2000 |
| WO | 01/35932 | 5/2001 |
| WO | 01/37804 | 5/2001 |
| WO | WO 01/35932 | 5/2001 |
| WO | WO 01/37804 | 5/2001 |
| WO | PCT/US02/02072 | 8/2002 |

OTHER PUBLICATIONS

Non-Final Office Action dated Jul. 3, 2006 in U.S. Appl. No. 10/341,142, filed Jan. 13, 2003 by Rasmussen.
Final Office Action dated Mar. 13, 2007 in U.S. Appl. No. 10/341,142, filed Jan. 13, 2003 by Rasmussen.
Non-Final Office Action dated Sep. 18, 2007 in U.S. Appl. No. 10/341,142, filed Jan. 13, 2003 by Rasmussen.
Non-Final Office Action dated Feb. 25, 2008 in U.S. Appl. No. 10/341,142, filed Jan. 13, 2003 by Rasmussen.
Non-Final Office Action dated Sep. 5, 2008 in U.S. Appl. No. 10/341,142, filed Jan. 13, 2003 by Rasmussen.
Final Office Action dated Apr. 20, 2009 in U.S. Appl. No. 10/341,142, filed Jan. 13, 2003 by Rasmussen.
Non-Final Office Action dated Nov. 9, 2009 in U.S. Appl. No. 10/341,142, filed Jan. 13, 2003 by Rasmussen.
Non-Final Office Action dated Oct. 6, 2005 in U.S. Appl. No. 10/322,143, filed Dec. 18, 2002 by Hansen.
Final Office Action dated Jul. 5, 2006 in U.S. Appl. No. 10/322,143, filed Dec. 18, 2002 by Hansen.
Advisory Action dated Jan. 22, 2007 in U.S. Appl. No. 10/322,143, filed Dec. 18, 2002 by Hansen.
Non-Final Office Action dated Oct. 31, 2007 in U.S. Appl. No. 10/322,143, filed Dec. 18, 2002 by Hansen.
Final Office Action dated May 8, 2008 in U.S. Appl. No. 10/322,143, filed Dec. 18, 2002 by Hansen.
Non-Final Office Action dated Sep. 29, 2008 in U.S. Appl. No. 10/322,143, filed Dec. 18, 2002 by Hansen.
Final Office Action dated Jul. 15, 2009 in U.S. Appl. No. 10/322,143, filed Dec. 18, 2002 by Hansen.
Non-Final Office Action dated Jan. 19, 2010 in U.S. Appl. No. 10/322,143, filed Dec. 18, 2002 by Hansen.
Non-Final Office Action Mailed Nov. 29, 2010 in U.S. Appl. No. 10/322,143, filed Dec. 18, 2002; First Named Inventor: Henrik Egesborg Hansen.
Written Opinion issued in connection with counterpart PCT Application No. PCT/DK01/00489, mailed Jun. 11, 2002.
International Preliminary Examination Report and accompanied Annex issued in connection with counterpart PCT Application No. PCT/DK01/00489, mailed Sep. 26, 2002.
Office Action issued in connection with counterpart European Application No. 01 960 172.3, mailed Mar. 2, 2006.
Office Action dated Jan. 29, 2008 in U.S. Appl. No. 11/052,645 by Buch-Rasmussen et al., filed Feb. 7, 2005.
Office Action dated Oct. 17, 2008 in U.S. Appl. No. 11/052,645 by Buch-Rasmussen et al., filed Feb. 7, 2005.
Final Office Action dated Jul. 15, 2009 in U.S. Appl. No. 10/322,143 by Hansen et al., filed Dec. 18, 2002.
A printout from <http://www.lk-online.dk/info_praeparat.asp?praeparatnr=2528>, (2003).
A search results listing all titles (pp. 1-3), (2003).
International Search Report issued in connection with counterpart International Application No. PCT/DK02/00865, mailed Apr. 10, 2003.
Written Opinion issued in connection with counterpart International Application No. PCT/DK02/00865, mailed Aug. 11, 2003.
International Preliminary Examination Report issued in connection with counterpart International Application No. PCT/ DK02/00865, mailed Mar. 13, 2004.
Office Action issued in connection with counterpart European Application No. 02787456.9, mailed Nov. 22, 2006.
Office Action dated Jan. 29, 2008 in U.S. Appl. No. 11/052,645, filed Feb. 7, 2005 by Buch-Rasmussen et al.
Office Action dated Oct. 17, 2008 in U.S. Appl. No. 11/052,645, filed Feb. 7, 2005 by Buch-Rasmussen et al.

DRY MOULDABLE DRUG FORMULATION

CROSS-REFERENCE TO RELATED PATENT APPLICATIONS

This patent application is a continuation of U.S. patent application Ser. No. 11/052,645, filed Feb. 7, 2005, which is a continuation of U.S. patent application Ser. No. 09/550,857, filed Apr. 17, 2000, which has been abandoned, and claims the benefit of Provisional U.S. Patent Application No. 60/139,403, filed Jun. 14, 1999, and Danish Patent Application PA 1999 00514, filed Apr. 16, 1999.

FIELD OF THE INVENTION

The invention concerns a long-term stable, solid, mouldable pharmaceutical composition for parenteral injection, a method for producing same, use of the composition as well as a device containing at least one composition.

BACKGROUND OF THE INVENTION

Injection of Solutions

By far the most widely used method for parenteral injection of drugs is by injection of an aqueous solution using a hypodermic syringe. The use of aqueous solutions is associated with a number of inherent problems. In order to inject a given volume of drug, a much larger volume of water and different additives also have to be injected. Weight ratios of drug to solvent may be in the range of 1:100 to 1:1,000. For intramuscular injection, the pain associated with injection is primarily caused by the volume injected, not by the penetration of the skin. Any reduction in volume would thus lead to a reduction in pain for the patient.

For some drugs, the solubility in water is very low. This has two consequences. Either the solutions become dilute and thereby the injection volume increases. Or, additives such as surfactants must be added to the solution to increase the concentration of active ingredient. Such additives or surfactants are potentially toxic. The potential for toxicity greatly limits the possibilities for developing formulations, thus potentially limiting the availability of important drugs.

Generally, an aqueous solution of any given drug is chemically less stable than a dry formulation of the same drug. Furthermore, an aqueous solution is prone to microbial contamination and needs to be sterilised by use of heat, radiation, filtration or chemical means. To increase the shelf life of aqueous drug formulations preservatives, stabilisers, antioxidants, biocides etc are often added. These additives may also add to the toxicity of the formulation. Alternatively or additionally, the aqueous solutions may require special storage conditions at low temperature to avoid chemical or microbial break down of the active ingredients and to avoid microbial growth.

For parenteral injection, the syringe needs to penetrate the epidermis or the mucosa. Whereas the tip of the syringe may be pointed and very thin, the presence of a hole provides it with a cutting edge which produces a micro-wound in the epidermis and thereby pain. Furthermore, for many patients, especially children, the pre-injection fear for pain is a factor to consider.

A considerable risk for hospital professionals as well as for sanitation workers is the risk of contamination from used hypodermic needles, which may carry infection. Patients may also be infected through multiple uses of needles.

Solid Dose Administration
Powder Injection

A number of publications deals with the task of injecting drugs formulated as solid microparticles. WO 94/24263 (Oxford Biosciences Ltd) discloses an apparatus for parenteral injection of particles or powders of a therapeutic agent. The therapeutic agent may be pure or mixed with a carrier, which will typically constitute less than 75%, preferentially less than 50% of the composition. Particles ranging from 0.1 to 250 µm in diameter are injected by means of a pressurised gas such as helium.

WO 96/03978 (Quadrant Holdings Cambridge Ltd) discloses a drug formulation in the shape of micro-fibres or micro-needles 1 to 150 µm in diameter and 5 to 150 µm long. The drug formulation may contain up to 20% active substance dispersed in an amorphous glassy matrix made from carbohydrate or carbohydrate derivatives. The preferred way of administering the formulation is through ballistic injection.

Due to the variation in particle size and shape, it is difficult to obtain a very precise penetration depth by powder injection. In parenteral injection, it is imperative to deliver the drug to the correct tissue, since drugs which do not penetrate the cutis are not taken up by the body, and since some drugs should reach the muscular tissue, some the subcutis and some the cutis to be transferred to the blood stream within a predetermined time limit. Energising means used for injecting the particles may include compressed gas, and explosives such as, propane, gasoline, or gunpowder. Such explosive means provides the apparatus for their administration with potential danger.

Implants

Solid dose drug formulations may also be administered by implantation. WO 93/10758 (Pitman Moore Inc) discloses such a sustained release formulation comprising an amorphous carbohydrate glass matrix, a biologically active therapeutic agent, and a hydrophobic substance which modifies the rate of release of the therapeutic agent from the glass matrix. This formulation may be in the shape of a rod extruded through a syringe and cut to lengths of 5 mm. These formulations comprise from 2 to 20% therapeutic agent. The carbohydrate glass matrix makes up between 60 and 90% of the formulation and is made from a mixture of one carbohydrate, a recrystallisation retarding agent and water. The formulations are intended for implantation but may also be administered orally.

WO 96/03978 (Quadrant Holdings Cambridge Ltd) (op.cit.) also encompasses macroscopic beads for subdermal implantation.

Whereas implants are excellent for sustained release they are not suitable for drugs, which have to be administered frequently, such as insulin or growth factors, or at varying time intervals, due to the need for medical assistance for their administration.

Needle Injection Systems

A few publications also deal with the task of administering a solid pharmaceutical composition having the shape of a needle or toothpick. Such formulations can be administered with greater precision than the abovementioned powders.

WO 96/08289 (Societe de conseils de recherches et d'application scientifiques S.A) discloses a device for parenteral administration of a medicament. The medicament has the shape of one end of a toothpick. Its dimensions range from 1 mm to 3 cm in length. The diameter may be up to 2 mm. The medicament comprises at least 50% active ingredient but may consist of 100% active ingredient without any carrier. Suitable water soluble carriers are e.g. hyaluronic acid, cellulose, polyalcohols, sugars, geletin, polyvinylpyrrolidone and starches. The carrier may also be water insoluble but biodegradable to provide sustained delivery. The medicament has a crush strength of 8 millipoise and is prepared using conventional techniques such as compression, thermofusion, or extrusion.

Macroneedles for injection are also disclosed in WO 96/03978 (Quadrant Holdings Cambridge Ltd). These needles are of the dimension 0.1 to 4 mm in diameter and 1 to 30 mm in length. The needles comprise a glassy vehicle and an effective amount of at least one guest substance. The glassy vehicle may comprise either a stabilising polyol or a hydrophobic carbohydrate derivative. The amount of guest substance may be up to 20% of the composition. The composition is disclosed as having sufficient compressive strength to be driven directly through the skin.

To obtain a satisfactory solid-dose-parenteral-injection, the composition to be injected must be of small volume to avoid injection pain and to achieve rapid dissolution. The small volume should be obtained by providing the composition with a strong carrier, whereby the amount of drug can be increased. The composition should be provided with a well-defined strength to make it possible to penetrate the cutis of the patient, be it an animal or human being. Furthermore, the composition should be long-term stable at ambient temperature in terms of both strength and structure of the composition and the biological activity of the drug. The carrier used to provide the necessary strength should comprise compounds that are tissue compatible and that are contained in the pharmacopoeia.

SUMMARY OF THE INVENTION

The present invention provides a solid pharmaceutical composition for parenteral injection comprising a binder and at least one therapeutic agent, said binder constituting at least 0.5% by weight of the composition and said binder comprising at least one binding agent being a carbohydrate, and optionally at least one non-crystallisation agent, whereby said binder forms an amorphous matrix and the amount of said therapeutic agent constituting at least one dosage.

By the term "at least one dosage" is meant that each composition, for example in the form of a pellet, comprises enough therapeutic agent for an average dosage, whereby the patient normally will inject one composition per administration.

Thereby, it is possible to provide a composition having sufficient strength for parenteral injection yet having a large content of therapeutic agent.

Furthermore the invention provides a method for preparing a solid pharmaceutical composition for parenteral injection comprising, mixing at least one therapeutic agent homogeneously with a binder, obtaining an amorphous melt matrix, whereby the binder comprises at least one binding agent being a carbohydrate and optionally at least one non-crystallisation agent, said binder constituting at least 0.5% by weight of the composition, shaping the melt to a predetermined geometry, cooling to below the Tg of the binder obtaining the composition, optionally removing the composition from the mould cavity.

According to an especially preferred embodiment, the melt is injected into a mould cavity having a predetermined geometry. It is a great advantage of this embodiment that it is possible to shape the composition by injection moulding, since methods for injection moulding are well developed and known to be industrially applicable. Injection moulding methods are used frequently for manufacture of plastic products such as syringes, filters, catheters etc. according to aseptic standards.

Another scope of the invention is to provide the use of a solid pharmaceutical composition as defined above for parenteral injection. The use of the compositions according to the present invention has many advantages over the prior art, especially for patients requiring frequent medication and for immunisation.

Finally the invention encompasses a device containing at least one solid pharmaceutical composition as defined above for parenteral injection, said device being adapted to inject the composition through epidermis or mucosa. The compositions can be moulded directly into this device which could be in the embodiment of a cartridge. Such a device provides very easy, rapid and essentially painless injection of the compositions.

BRIEF DESCRIPTION OF THE DRAWINGS

The patent or application file contains at least one drawing executed in color. Copies of this patent or patent application publication with color drawing(s) will be provided by the Office upon request and payment of necessary fee.

DETAILED DESCRIPTION OF THE INVENTION

The Composition

Figure 1:
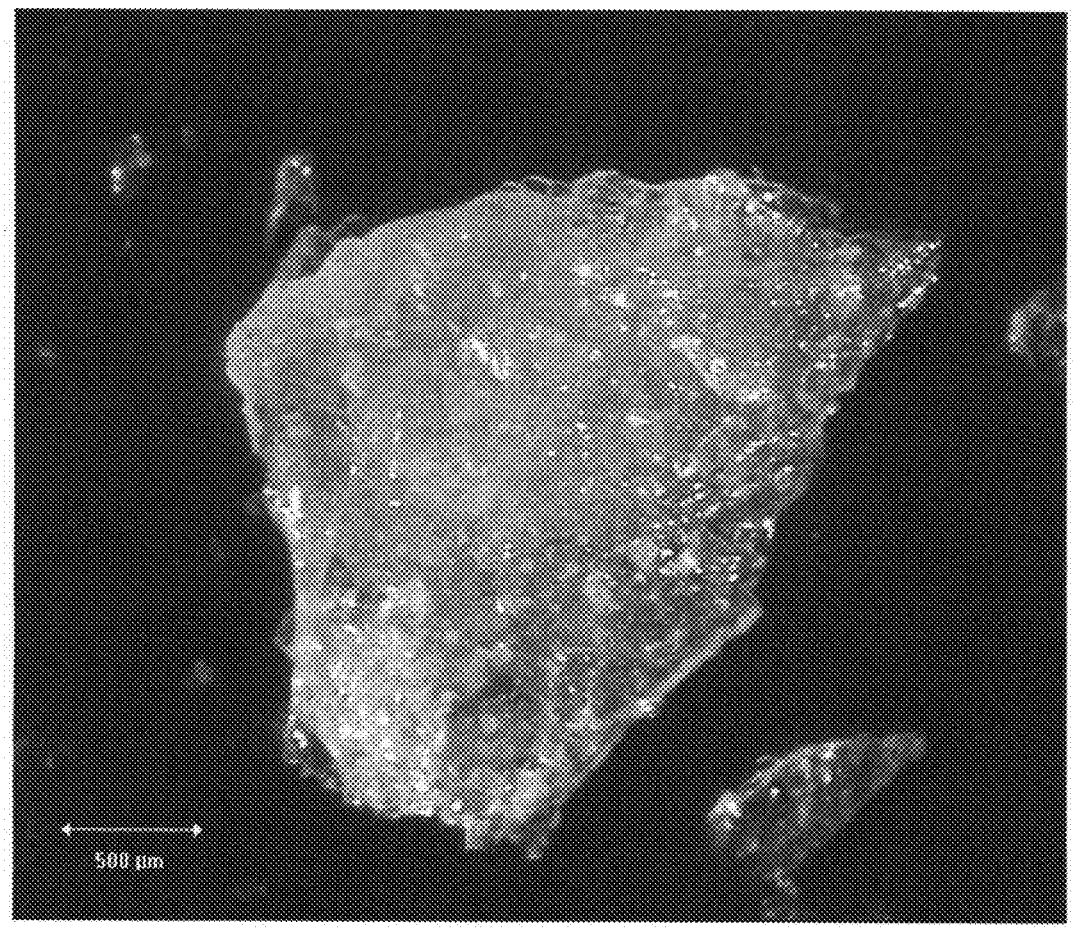
FIG. 1 is a photograph of a cooled mixture of 50% dry amorphous C*Maltidex H16323 with 50% human insulin.

The invention relates to a solid pharmaceutical composition for parenteral injection, a method for preparing the composition, use of the composition for parenteral injection as well as a device containing at least one solid pharmaceutical composition for parenteral injection.

According to the invention, a solid pharmaceutical composition for parenteral injection is provided. The composition comprises a binder and at least one therapeutic agent, said binder constituting at least 0.5% by weight of the composition and said binder comprising at least one binding agent being a carbohydrate, and optionally at least one non-crystallisation agent, whereby said binder forms an amorphous matrix.

By the present invention, it is possible to provide a composition having sufficient strength for parenteral injection yet having a large content of therapeutic agent. The binder is in a state of an amorphous matrix, which could also be termed an amorphous glassy matrix or a glass. The binder is present in an amount sufficient to produce, in combination with the therapeutic agent, the required strength of the composition. Therefore, the binder may constitute at least 1% by weight of the composition, such as at least 5% by weight of the composition. Mostly the binder may constitute at least 5% and at most 60% by weight of the composition.

Important is also that the therapeutic agent is distributed homogeneously throughout the composition. One consequence of this is that the strength is also homogenous throughout the composition. Another consequence is that the therapeutic agent is liberated at the same rate as the binder dissolves after injection.

In addition to the strength, the binder also provides the composition with a very smooth surface. Thereby, the friction upon penetration of the epidermis or mucosa is greatly reduced and consequently less force is required for the penetration and the penetration causes less pain. It is to be specifically understood that the composition penetrates the epidermis or the mucosa of the patient without the aid of any kind of syringe or trocar or similar devices. An advantage is that the composition is very stable both in terms of the biological activity of the therapeutic agent and in terms of the geometry and the strength of the composition even when it is stored at ambient temperature. Thereby, the invention combines compactness with ease of storage. Thus, patients requiring frequent parenteral medication, such as diabetics, growth deficiency patients and hemophilics, can store and carry their drugs much like tablets in a glass, a blister package, or in a cartridge containing the drugs.

According to an especially preferred embodiment, the binder essentially remains an amorphous matrix for at least 6 months at ambient temperature. This is achieved by carefully selecting the binding agent and the optional non-crystallisation agent so that the binding agent does not crystallise during storage. If the binding agent starts crystallising the composition will lose its strength, or if the crystallisation only takes place at the surface, the geometry of the composition will change and the friction upon injection will increase undesirably.

By the term strength is meant that the composition has sufficient compressive strength to penetrate the skin of a patient. It has been determined experimentally that a pressure force of less than 5 Newton is required to penetrate the epidermis of a human being with the claimed composition. Less is required to penetrate the mucosa. Consequently, the composition must be able to withstand such pressure force.

The strength can be tested in a force gauge tester such as an Advanced Force Gauge AFG-250N from Mecmesin, UK. Tests are carried out by formulating the composition as a rod and applying a pressure force to the rod. The pressure force is increased until the rod breaks. The instrument records the pressure force necessary to break the rod. This parameter is termed the compressive strength and should be understood as the breaking strength under compression.

According to a preferred embodiment, a rod made from the binder alone is able to withstand a pressure force of at least 10 Newton. According to another embodiment, a rod made from the composition is able to withstand a pressure force of at least 5 Newton. Thereby, the composition has a well-defined compressive strength, which is furthermore sufficient to endure the force required to penetrate the epidermis.

Furthermore, at least 95% of the strength of the composition may be maintained after 6 months, preferably after 12 months, at ambient temperature. It is important that the compositions are long term stable not only with respect to the biological activity and the structure of the composition, but also that the strength is essentially unaffected by storage. Some binding agents have a propensity to slowly crystallise after the amorphous glass matrix has been formed. Such binding agents are unsuitable for the present invention.

Preferentially, the composition should be essentially free from entrapped air. It is very important for the strength of the composition that no air is trapped inside the composition during processing in order to prevent air in the composition after cooling. Apart from reducing the strength, entrapped air also takes up unnecessary space and thereby reduces the amount of therapeutic agent contained in the composition.

The composition preferentially has the shape of a pellet wherein the cross section of the pellet is substantially cylindrical, triangular, square, or polygonal. According to an especially preferred embodiment, the composition has the shape of a rod essentially cylindrical and pointed at one end. With compositions according to these embodiments, it becomes especially important to withstand crystallisation.

As a human skin model, porcine abdomen skin has been used in penetration tests. Graphite rods with differently shaped pointed ends are pressed into porcine skin with a Lloyd Instrument LR5K, UK. The pressure force is measured in Newton as a function of the distance. The maximum force is used to compare the different rod shapes. No point (180°) on the rod is unsatisfactory and the rod breaks before entering the skin. Using a graphite rod with a cone shaped point (90° top angle) is sufficient to penetrate the skin. However, a top angle of 60° significantly improves the penetration of the skin. The rod is preferably as pointed as possible, however, points with an angle below 10° are very thin and thereby fragile. The top angle of the pointed end should preferably be between 10 and 110°, preferably between 20 and 90°, more preferably between 30 and 70°.

The top radius of the tip is preferably below half of the diameter of the composition as such, more preferably below a fourth of the diameter of the composition as such.

By this embodiment is obtained that the composition acts like a needle and can penetrate the cutis or mucosa of the patient in the same way as a hypodermic needle to enter the subcutis or submucosa. Thereby less force is required to force the composition through the cutis or mucosa and less binder is required to obtain the necessary strength. With less binder, the compositions can contain relatively more therapeutic agent.

When the composition has the shape of a needle it is especially important the composition remains stable and does not crystallise. The delicate tip of the needle would easily be destroyed through crystallisation of the binding agent.

The composition may have a maximum cross section of less than 1 mm, preferably from 0.7 to 0.3 mm, more preferably 0.6 to 0.4 mm. By providing the composition with this thickness, it has been determined that it can be injected essentially without pain. A further advantage is that less force is required to penetrate the skin as the diameter is reduced. By needles formed of the composition according to the invention, it has been found that even at these dimensions they still have the necessary strength to penetrate the cutis or mucosa upon injection. A further advantage of using small diameters is that the surface area to volume ratio is higher than for larger diameters. Thereby the compositions are dissolved more rapidly and the drugs can enter the body fluids to exert their effect. However, a too small diameter will require a very long composition in order to contain the predetermined amount of therapeutic agent. A too small diameter would also reduce the compressive strength of the composition and maybe cause it to break upon injection.

The composition is preferably in the form of a pellet. The cross section of the pellet may be substantially cylindrical, triangular, square or polygonal.

The composition may be manufactured in any length but for most applications, the length of the rod is less than 10 mm, preferably less than 8 mm, more preferably less than 6 mm. The length of the composition is determined by the dose of the therapeutic agent, the amount of binder, and the selected diameter. The dose of many therapeutic proteins is approximately 1 mg. One mg of protein excluding binder corresponds approximately to a cylinder with a diameter of 0.5 mm and a length of 3 mm. If such a composition containing 1 mg of protein is made from 50% therapeutic agent and 50% binder, the composition has a length of 6 mm. When the required dose is smaller, the dimension of the composition will be reduced accordingly. A dose of ⅓ mg protein in a composition with 50% binder having a diameter of 0.5 mm has an approximate length of 2 mm. The invention is not restricted to any specific volume, the volumen being determined by the length and diameter of the composition. In most cases, the volume of the composition is less than 5 µl, preferably less than 1 µl. Volumes down to 0.25 µl can obtained for small doses of therapeutic agent. Thus, the above-mentioned composition having a diameter of 0.5 mm and a length of 2 mm has a volume of 0.39 µl.

In particular when the daily dosage of the therapeutic agent is 1 mg or more, the therapeutic agent may comprise at least 25% by weight of the composition, preferably more than 30%, more preferably more than 40%. One of the great advantages of the invention is that it is possible to obtain compositions having a very large content of therapeutic agent since the binder is strong enough to provide the strength and geometry of the composition even when present in relatively small quantities.

The invention encompasses compositions, wherein the therapeutic agent comprises up to 95% by weight of the composition. This has been determined as the maximum amount of therapeutic agent that can be loaded into the composition without reducing the compressive strength below the required limits.

According to an especially preferred embodiment of the invention, the binder comprises at most 80% by weight, such as at most 60% by weight, preferably at most 50% by weight of the composition, more preferably at most 40%.

In another embodiment wherein very potent therapeutic agents are used, such as wherein the dosage is 1 µg or less, the therapeutic agent may constitute less than 20% by weight of the composition such as less than 10% by weight, more preferably less than 5% by weight of the composition.

Thereby, the binder comprises about at least 80% by weight of the composition, preferably at least 90% by weight of the composition, more preferred at least 95% by weight of the composition.

A composition comprising a potent therapeutic agent is preferably having a volume below 0.25 µl, such as below 0.1 µl, or even below 0.01 µl.

The at least one binding agent which together with the optional at least one non-crystallisation agent comprises the binder, may comprise from 50 to 97% by weight of the binder. The preferred amount of binding agent is determined by numerous factors, primarily the actual compound chosen. Some binding agents may form the amorphous glassy matrix of the binder in a pure state and others will need to be mixed with the non-crystallisation agent in various amounts.

When present, the at least one non-crystallisation agent may comprise at least 1% by weight of the binder. In some cases very limited amount such as down to 1% of non-crystallisation agent needs to be present to prevent crystallisation of the binding agent. The amount of non-crystallisation agent is determined largely by the propensity of the binding agent to crystallise.

Many compounds are capable of forming a glass upon melting and subsequent quenching to below the glass transition temperature of the compound, Tg. Glasses can also be formed by dissolution and subsequent removal of the solvent, whereby the Tg is raised to above the storage and usage temperature. However, most compounds have a propensity to crystallise by themselves. Whereas an amorphous glass matrix often has a high compressive strength and a smooth surface, the same compound in a crystalline state has very limited compressive strength and a rough surface. The present inventors have determined that compositions can be made from pure maltose or from pure sorbitol. These compounds will form glasses, but the compounds crystallise gradually at room temperature causing the strength to be reduced and the geometry to be changed. By mixing two or more compounds, crystallisation can be prevented or retarded. The exact proportion of the two compounds necessary to prevent crystallisation must be determined in each specific case.

The compositions are not necessarily completely water free. However, the water content of the binder is less than 20% (w/w), preferably less than 10%, more preferably less than 5%, such as from 0.1 to 5%, preferably from 1 to 5%. It has been determined that by having a water content between 0.1 and 5%, the composition is not sticky and the binder is dissolved rapidly once injected. By lowering the water content even further, the rate of dissolution upon contact with the body fluids may be reduced disproportionately causing the therapeutic agent to be released only very slowly. Furthermore, many therapeutic agents such as proteins, peptides and polypeptides are more stable at a low water content than when completely dry. The advantage of having a low water content is that the therapeutic agent becomes biologically very stable and does not require special storage conditions such as refrigeration to maintain the biological activity. A third advantage is that the composition becomes essentially resistant to microbial attack, since microbes require a certain water content in order to establish a colony. Thus the requirement for handling the compositions become less rigid since the presence of a few microbes on the composition will not result in microbic proliferation and thereby not cause contamination. Finally the presence of excess water in the composition may result in water vapour during processing, which may give rise to air entrapment in the composition during subsequent cooling.

Several compounds may be used as the at least one binding agent and the invention is not limited to any specific compounds. According to a preferred embodiment the at least one binding agent is a mono-, di-, or oligosaccharide or a corresponding sugar alcohol or a derivative thereof. Many of these compounds are frequently used for drug formulation, are contained in the pharmacopoeia and can therefore readily be approved by the authorities. Furthermore, these compounds make an amorphous glassy matrix readily.

Furthermore, the at least one binding agent may be a carbohydrate-derivative. As mentioned, carbohydrates make amorphous glassy matrices readily. In some cases it is preferred to provide the composition with a binder having a slow rate of dissolution compared to binder made from true carbohydrates. This can be obtained by derivatising the carbohydrate, especially by adding non-polar groups to the carbohydrate, whereby the compound is rendered more hydrophobic.

According to a preferred embodiment the at least one binding agent is selected from maltose, sucrose, lactose, cellobiose, trehalose, maltulose, iso-maltulose, maltitol, sorbitol, mannitol, glucose, fructose, raffinose, melezitose, dextran, man nose, sorbose, melibiose, sophrose, turanose, lactulose, stachyose. This group of carbohydrates has excellent amorphous glass matrix making abilities. Furthermore, the carbohydrates are well known and can be purchased at reasonable price and in well characterised grades.

The optional at least one non-crystallisation agent may preferentially also be a carbohydrate, said carbohydrate being different from the binding agent. Likewise, the non-crystallisation agent may be a mono-, di-, or oligosaccharide, a corresponding sugar alcohol, or a derivative. It may be a natural or synthetic carbohydrate and according to an especially preferred embodiment the at least one non-crystallisation agent is selected from maltose, sucrose, lactose, cellobiose, trehalose, maltulose, iso-maltulose, maltitol, sorbitol, mannitol, glucose, fructose, raffinose, melezitose, dextran, mannose, sorbose, melibiose, sophrose, turanose, lactulose, stachyose.

Each combination of binding agent and non-crystallisation agent gives a unique amorphous glass matrix with a unique glass transition temperature, unique solubility, and unique strength. The composition has been found to perform excellently when the binding agent is selected from maltitol, sucrose, sorbitol, and mannitol and the non-crystallisation agent is selected from sorbitol, maltitol, and mannitol. These compounds are often used for pharmaceutical compositions, they all have the advantage of being edible and without any side effects upon administration.

According to an especially preferred embodiment, the binding agent is maltitol and the non-crystallisation agent is sorbitol and/or hydrogenated oligosaccharides. By using these specific compounds to make up the binder, especially excellent results are obtained since the obtained amorphous glass matrix has an optimal glass transition temperature and since the propensity to crystallise is very low. Furthermore, maltitol can be obtained in quantities and in a very suitable grade. Commercial maltitol is made by enzymatically degrading starch whereby a mixture of glucose, maltose, maltotriose and higher saccharides are formed. These are hydrogenated to form their corresponding sugar alcohols sorbitol, maltitol and hydrogenated oligosaccharides. Thus, the product contains primarily maltitol and sufficient amounts of the other sugar alcohols to prevent the crystallisation. Maltitol is tissue compatible, it is a well tested compound and has been used for years in the production of so-called sugarfree candies.

The binder comprising the at least carbohydrate and the optional at least one non-crystallisation agent should not reduce the stability of the therapeutic agent. This could for instance take place via chemical reactions between the therapeutic agent and the components of the binder, either during processing or during storage. To avoid undesired reactions between aldehyde groups in reducing sugars and side chains of proteins, peptides, or polypeptides, the at least one carbohydrate and the at least one non-crystallisation agent are preferentially chosen from the group of non-reducing sugars.

The Tg of the binder in the final composition should preferably be at least 30° C. The Tg of the binder should be above ambient temperature, preferably 5 to 10° C. above ambient temperature, or the composition will gradually melt during storage. Under certain special conditions, it may be necessary to select a binder having a higher Tg, e.g. for use in the tropics. With certain very heat labile therapeutic agents, it may be necessary to select a binder having a much lower Tg, so that the composition can be processed at e.g. 50° C. With such a low Tg, it may be necessary to store the compositions cold at 5° C. and to inject them before the temperature rises above the Tg.

The invention is not limited by an upper Tg of the binder. Binders having a Tg from 40 to 120° C. are preferred. Depending on the therapeutic agent, it is preferred that the Tg of the binder is less than 90° C., more preferably less than 80° C. A majority of therapeutic agent are heat labile and although many proteins or peptides can tolerate exposure to elevated temperatures in a dry state a loss of activity may nevertheless be encountered during processing. To reduce exposure of the therapeutic agent to elevated temperatures it is therefore preferable to select binders with a low Tg with due respect to the lower limits mentioned above.

According to a preferred embodiment, the viscosity of the composition is less than 50,000 Pa*s, preferably less than 40,000 Pa*s, more preferably from 1,000 to 30,000 Pa*s, in a sub-range of the temperature interval between 60 and 140° C. In this temperature interval the composition is in the state of a melt, which can be shaped. Generally, most glasses encompassed by the present invention have a suitable viscosity for bringing into the desired geometry at 20 to 30° C. or even approximately 40° C. above Tg of the binder. The viscosity of the composition is very important during injection of the melt into the mould and furthermore in the embodiments where the therapeutic agent is mixed with the melted binder.

The composition may also be injection mouldable in a sub-range of the same temperature interval. A preferred method for manufacturing the composition is by injection moulding. This means that the composition should possess a certain viscosity e.g. 1,000 to 30,000 Pa*s in at least a sub-range of the temperature interval 60 to 140° C.

As described above the composition may be provided with different dissolution rates according to the type of carbohydrate selected for the binder. Preferentially, however, at least 50% of the therapeutic agent should be released from the composition within 1 hour after injection. This is obtained by selecting the at least one carbohydrate and the optional non-crystallisation agent from the group of polar compounds and by keeping the water content of the composition within the preferred limits.

Any type of therapeutic agent can be incorporated into the composition and the invention is not limited to drugs with any specific function. Thus the therapeutic agent may be selected from analgesics, antianxiety drugs, antiarthiritic drugs, antibiotic agents, anticholinergics, antidepressants, antidiabetics, antiemetics, antihistaminics, antihypertensive agents, antiinflammatory drugs, antimigraine agents, antiparkinsonism agents, antipasmodesics, antipsychotics, antithrombotic agents, antiviral agents, appetite suppressants, blood factors, cardiovascular drugs, cerebral vasodilators, chemotherapeutic drugs, cholinergic agonists, contraceptives, coronary agents, diuretics, growth factors, hormonal agents, immunosuppressive agents, narcotic antagonists, opiods, peripheral asodilators, tranquilizers, vaccines, immunogenic agents, and immunising agents.

Similarly, the therapeutic agent may be any type of compound such as steroids, hormones, lipids, nucleic acids, nucleotides, oligonucleotides, oligosaccharides, organics, antibodies, peptide mimetics, peptides, polypeptides, polysaccharides, and proteins. In particular the therapeutic agent may be a peptide, a polypeptide or a protein. Actually, the composition may also contain subcellular compositions, cells, bacteria or vira as a therapeutic agent for immunogenic purposes.

These compounds may be soluble in the amorphous glass matrix or they may be dispersed therein as particles. Important is that the therapeutic agent is homogeneously distributed throughout the composition so that its release is initiated as soon as the composition starts dissolving.

In the embodiments, where the therapeutic agent is selected from proteins, peptides, and polypeptides, the protein, peptide, or polypeptide may be either amorphous or crystalline.

According to a preferred embodiment, the therapeutic agent is selected from hormones, antidiabetic drugs, growth factors, and blood factors. Preferably, the therapeutic agent is a protein selected from the group insulin, glucagon, growth hormone, growth factors, blood factors such as FVII or FVIII, GLP-1, EPO, TPO, interferon or derivatives of these proteins. Such proteins can either be naturally occurring proteins or recombinant proteins.

Apart from the binder and the therapeutic agent, the composition may comprise additives, which could be selected from but is not restricted to the group of preservatives, stabilisers, adjuvants, lubricants, and disintegraters. Some therapeutic agents may need to be preserved or stabilised through the use of a preservative or stabiliser, although this is likely to be necessary only in a few cases, owing to the almost anhydrous conditions in the composition. In the cases where the therapeutic agent is for immunisation, it may be preferential to add an adjuvant to increase the immunogenic response. Lubricants such as fatty acids or their salts may be added to ensure that the composition does not stick to its packaging, e.g. a cartridge, and/or to provide lubrication as the composition penetrates the skin. Lubricants may be stearates, such as Mg-stearates, Zn-stearates, or Ca-stearates. In cases where a rapid release of the therapeutic agent is desired and in cases where the therapeutic agent comprises a large proportion of the composition it may be necessary to add disintegrators which will cause the composition to disintegrate and thereby release the therapeutic agent rapidly.

Furthermore, the composition may be provided with a coating. Such a coating could for instance comprise a lubricant as mentioned above and the purpose could for instance be to reduce the friction during penetration of the epidermis and thereby reduce the injection pain.

Methods for Preparing the Composition

In addition, the invention provides a method for preparing a solid pharmaceutical composition for parenteral injection comprising, mixing at least one therapeutic agent homogeneously with a binder, obtaining an amorphous melt matrix, whereby the binder comprises at least one binding agent being a carbohydrate and optionally at least one non-crystallisation agent, said binder constituting at least 0.5% by weight of the composition, shaping the melt to a predetermined geometry, cooling to below the Tg of the binder obtaining the composition, optionally removing the composition from the mould cavity. The term "amorphous malt matrix" means that at least the binder is amorphous in the melt.

The disclosed method provides a simple and industrially applicable method for the preparation of the compositions.

According to an especially preferred embodiment, the melt is injected into a mould cavity having a predetermined geometry. It is a great advantage of this embodiment that it is possible to shape the composition by injection moulding, since methods for injection moulding are well developed and known to be industrially applicable. Injection moulding methods are used frequently for manufacture of plastic products such as syringes, filters, catheters etc. according to aseptic standards.

The exact order of the steps may be varied according to the invention. Thus the amorphous glass matrix constituting the binder may be produced in larger quantities and stored for later processing or disintegrated and stored, or processed immediately.

Different methods for producing the amorphous glass matrix may also employed. The binder can be melted and quenched to make the amorphous glass matrix. The binder can be dissolved in a suitable solvent, preferentially in water, and the solvent removed by various methods such as boiling, vacuum boiling, freeze drying, spray drying, vacuum evaporation, air drying, or fluidised bed drying. Upon removal of the solvent, the binder will form an amorphous glass matrix for further processing.

Similarly, the therapeutic agent may be added at different points of the process. Preferentially it is added when the binder is in the state of a dry powder as mentioned above, but it may also, where appropriate, be kneaded into the melted binder. It may also be added to a solution of the binder and be dried or melted together with the binder. The choice of method will depend primarily on the glass forming temperature of the binder and the ability of the therapeutic agent to withstand elevated temperatures.

In a preferred embodiment, the therapeutic agent is dissolved in a solution and then mixed with a solution of the binder. The mixed solutions may then be dried, shaped, optionally preceded by a drying step.

According to one embodiment, the binder is brought into a solid amorphous glass matrix by dissolving in a solvent and drying, preferentially by freeze-drying. After preparing the amorphous glass matrix, the matrix can be processed into a powder by known methods.

According to an especially preferred embodiment, the binder and the at least one therapeutic agent are mixed homogeneously as powders. An advantage of this embodiment is that the therapeutic agent and the binder can be mixed in an essentially dry state where both ingredients are in the shape of a powder. Mixing under these conditions is performed very easily. Experiments have shown that it may be difficult to obtain a homogeneous mixture when the therapeutic agent is added to the binder in a molten condition and for instance kneaded into the binder at least when produced in small amounts. An additional advantage of mixing in the dry state is that mixing can take place at ambient temperature whereby the activity of the therapeutic agent is conserved. When the composition has been mixed, it is melted and can immediately be injection moulded whereby prolonged exposure of the therapeutic agent to elevated temperatures is avoided.

The binder should contain less than 20% water by weight, preferably less than 10%, more preferably less than 5%, such as from 1 to 5%. A melt consisting of for instance glucose and sucrose can contain up to 20% water by weight and still not boil at 110° C. It is important that the binder does not boil during processing, when heating is the preferred way of preparing the amorphous glass matrix. Boiling is an indication of excess water, which may destabilise the therapeutic agent if it is present at this stage. Moreover, boiling water will create bubbles in the composition resulting in air entrapment. It is also important to bear in mind that the water content of the composition should not change during injection moulding and cooling of the composition. Whatever water is present in the composition during moulding should remain inside it and not for instance condense on the surface of the composition, since this may cause dissolution of parts of the composition.

After the composition has been cooled in the mould cavity, it may optionally be removed and packaged in a blister package, in an injection cartridge or in a glass.

Use of the Composition

The invention also encompasses the use of a solid pharmaceutical composition for parenteral injection, said solid pharmaceutical composition comprising a binder and at least one therapeutic agent, said binder constituting at least 0.5% by weight of the composition and said binder comprising at least one binding agent being a carbohydrate, and optionally at least one non-crystallisation agent, whereby said binder forms an amorphous matrix.

There are several advantages connected with using a solid pharmaceutical composition according to the invention for partenteral injection. Through avoidance of needles, one source for cross contamination in hospitals is eliminated. The injection volume according to the invention is very small, it can be less than 5 μL, preferably from 1 to 2 μL. Therefore, the composition can be injected essentially without pain.

In addition, the therapeutic agent of the composition according to the invention is long term stable even at ambient temperature and there is no need for special storage conditions such as refrigeration. Furthermore, the composition is stable at ambient temperature both in terms of the compressive strength, the glassy nature of the binder and the geometry.

It is expected that the invention can be used for any kind of animal, which needs medication through parenteral injection. Such animals could for instance include fish, birds, molluscs, reptiles, or mammals including man.

The composition can preferably be used for patients requiring frequent medication such as diabetics. By frequent is meant that the therapeutic agent must be injected parenterally at least once a day. Such patients always need to carry with them a quantity of therapeutic agent for injection. The convenience of administration as well as the convenience of storage of the compositions according to the present invention makes it especially useful for this group of patients.

Another preferred use of the composition is for immunisation. Immunisation of children is often carried out in the clinics of general practitioners that will appreciate the less rigid storage requirements of the compositions according to the inventions. The same cartridge containing several compositions can be used for different children, since there is no risk for cross contamination. The only object that penetrates the skin of the patient is the composition itself. The injection will not cause the injection device or the cartridge housing the compositions to be contaminated. Additionally, children who often suffer from pre-injection fear will appreciate the almost painless injection that can be carried out.

Another large group of patients requiring immunisation is in the tropics and during epidemics where large groups of individuals need immunisation at essentially the same time. Using the compositions according to the present invention for mass immunisations is much more rapid and much safer than using conventional injection of aqueous solutions or suspensions of the immunoactive agent. According to the prior art, a new hypodermic needle needs to be used for every single person.

Mass medication is also frequently used in animal and fish farming. In these cases it will also be of great advantage to use the compositions according to the present invention for reasons of speed and reduction of cross contamination.

A Device Containing the Composition

The invention also encompasses a device containing at least one solid pharmaceutical composition for parenteral injection, said solid pharmaceutical composition comprising, a binder and at least one therapeutic agent, said binder constituting at least 0.5% by weight of the composition and said binder comprising at least one binding agent being a carbohydrate, and optionally at least one non-crystallisation agent, whereby said binder forms an amorphous matrix, said device being adapted to inject the composition through epidermis or mucosa.

This device could for instance be in the embodiment of a cartridge where the compositions are stored for later injection. It is of course also possible to manufacture the composition directly in the cartridge so that there is no need for handling the compositions after they have been injection moulded and hardened. Preferentially the cartridge is sealed by a suitable sealing means after the compositions have been moulded and cooled to below Tg of the binder. This seal protects the compositions from humidity and contamination. Such a cartridge also forms a convenient storage and shipping means to protect the delicate compositions during storage and shipping. Optionally, the cartridge can be fitted directly on an injection device adapted to inject the compositions parenterally.

EXAMPLES

In the following, the invention is described as non-limiting examples.

Example 1

Extruded Composition Containing 100% Human Insulin (Comparative Example)

1.0 g of insulin is mixed with 1.0 g of water. The mixture was kneaded with a spatula in a glass bottle until homogeneity. The mixture was placed in a Ray-Ran test sample moulder from Ray-Ran Engineering, UK. The mixture was extruded through a 0.5 mm hole. The resulting rods were dried for 24 hours. The compressive strength was tested with an Advanced Force Gauge AFG-250N from Mecmesin, UK. The compressive strength of the rods (diameter 0.5 mm, length 5 mm) was between 2 and 5 N and the rods were therefore not able to penetrate human skin. The rods were investigated under microscope and air entrapment was observed.

Example 2

Extruded Composition Containing 80% Human Insulin and 20% Mannitol (Comparative Example)

0.4 g of mannitol was dissolved in 3.6 g water. 1.6 g of insulin is mixed with the mannitol solution. The mixture was kneaded with a spatula in a glass bottle until homogeneity. The mixture was placed in a Ray-Ran test sample moulder from Ray-Ran Engineering, UK. The mixture was extruded through a 0.5 mm hole. The resulting rods were dried for 24 hours. The compressive strength was tested with an Advanced Force Gauge AFG-250N from Mecmesin, UK. The compressive strength of the rods (diameter 0.5 mm, length 5 mm) was between 1 and 5 N and the rods were therefore not able to penetrate human skin. The rods were investigated under microscope and air entrapment was observed.

These examples illustrate that compositions with the same size and shape as the compositions according to the present invention but without a binder in the state of an amorphous matrix do not have the physical strength to be parenterally injected. One of the reasons for the lack of strength is the presence of entrapped air. Thus, such compositions will need to be injected by use of a hypodermic needle, a trocar or similar means. Thereby, they do not have the advantages of the present invention.

Example 3

Composition Comprising a Binder, 100% C*Maltidex® H16323 (88% maltitol)

100 g C*Maltidex® H16323 (88% maltitol) was cooked at 168° C. with 8 minutes vacuum time in the end. The solution was cooled to 100° C. and transferred to the Ray-Ran test sample moulder from Ray-Ran Engineering, UK and extruded through a 0.5 mm hole. The amorphous glassy rod was cooled to room temperature. The compressive strength was tested with an Advanced Force Gauge AFG-250N from Mecmesin, UK. The compressive strength of the rods (diameter 0.5 mm, length 5 mm) was between 30 and 50 N and therefore suited to penetrate human skin. Thus the compressive strength of the dry C*Maltidex® (88% maltitol) rods are comparable with the HB type pencil from Pentel, Japan.

This example illustrates that it is possible to manufacture compositions according to the present invention with a very large strength. In the specific example a composition was moulded from C*Maltidex® (88% maltitol). This product contains in itself sufficient "impurities", primarily sorbitol and sugar alcohols of maltotriose and higher oligosaccharides, acting as non-crystallisation agents.

Example 4

Composition Comprising 50% Binder 50% Insulin 35 g of dry amorphous C*Maltidex® H16323 (88% maltitol) was mixed with 35 g human insulin in a Brabender with a Plasti-Corder PL2000 and Mixer Measuring Head at 95° C. until the torque in Nm was constant. The mixture was cooled and investigated under microscope and there was no air entrapment, which also is indicated by the constant torque. The activity of insulin was measured before and after the mixing at 95° C. using the pharmacopoeia HPLC method. FIG. 1 shows the cooled mixture having no air entrapment. The insulin activity before mixing was 99,62% and after mixing 97,52%. The difference is not significant.

The example illustrates the advantage of preparing a composition without adding water. Although the melt is prepared at 95° C., the reduction in insulin activity is negligible. This is primarily a consequence of the almost anhydrous state of the glass matrix. Many heat labile therapeutic agents, typically proteins, polypeptides and peptides, tolerate relatively high temperatures in the absence of water.

Example 5

Compressive Strength of a Composition

The mixture prepared in example 4 was transferred to the Ray-Ran test sample moulder from Ray-Ran Engineering, UK and extruded through a 0.5 mm hole at 100° C. The amorphous glassy rod including the dry drug filler was cooled to room temperature. The compressive strength was tested with an Advanced Force Gauge AFG-250N from Mecmesin, UK. The compressive strength of the rods (diameter 0.5 mm, length 5 mm) was between 10 and 40 N and therefore suited to penetrate human skin.

The composition according to this example contains 50% by weight of both therapeutic agent and amorphous binder. The compressive strength of the rods is satisfactory.

Example 6

Preparation of Freeze-dried Maltitol/insulin Composition 7 g of dry insulin was dissolved in 125 ml distilled water to about 5% solids in water, giving a pH of 4.5-4.6. The sample had a milky appearance the pH was adjusted to 9 with NaOH after which is was held at 5 C for 3 hours with weak stirring. The sample still had a milky appearance. The pH was then adjusted to 7.4 and held at 5 C for 3 days with stirring and then 1 day without stirring. At this time, the sample appeared opalescent with white "fluff". The sample was divided into 4 portions, and to each portion 2 g maltitol (C*Maltidex® H 16323 (88% maltitol), Celestar Scandinavia NS, 043/ 10092364) having a high content of dry solid was added, whereafter the final solutions were stirred.

The freeze-drying was conducted as a 3.5 day drying of the following conditions:
Freezing: 3 hrs at −45° C.
Primary dry: 24 hs at −20° C., 0.1 hPa
24 hs at −50° C., 0.1 hPa
Secondary dry: 36 hrs at 25° C., atmospheric After freeze-drying insulin/maltitol powder was obtained, said powder being ready for being melted into an amorphous melt matrix with therapeutic agent.

Example 7

Preparation of Composition from Freeze-dried Powder

Figure 2:
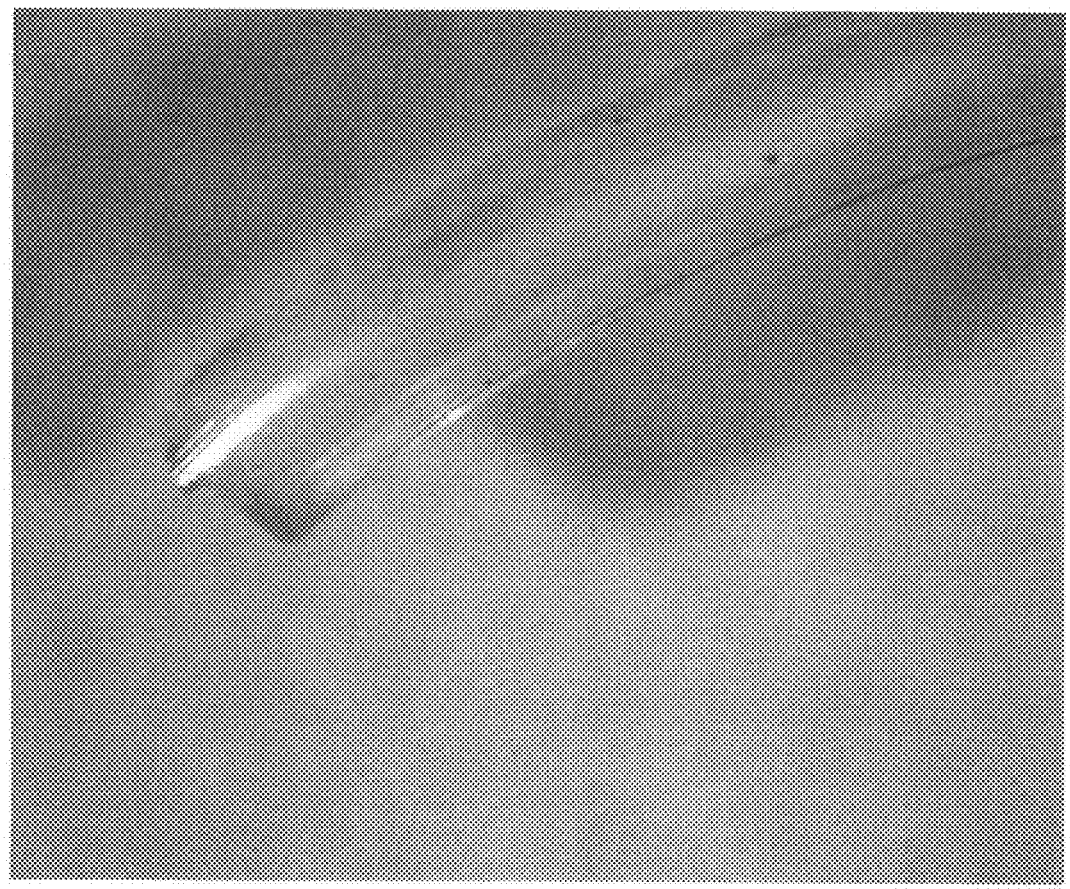
FIG. 2 is a photograph of an extruded glassy rod obtained from freeze-dried insulin/Maltitol powder.

The freeze-dried powder from example 6 was heated to 140° C. and extruded as shown in Example 5. The amorphous glassy rod including insulin was cooled to room temperature. The rod obtained is shown in FIG. 2, wherefrom the transparency and smooth surface is apparent. The magnification is 70:1. The compressive strength of the tested rods (diameter 0.5 mm, length 5 mm) was between 20-45N.

Example 8

Injection Moulding Composition

Figure 3:
FIG. 3 is a photograph of an injection moulded composition (50% binder and 50% insulin) having a diameter of 0.5 mm with a tip angle of 30 degree.

The composition obtained in Example 4 was extruded at a temperature of 100° C. and moulded in a mould having a temperature of 60° C., whereafter the composition was cooled. The injection moulded composition is shown in FIG. 3 having a diameter of 0.5 mm with a tip angle of 30 degree.

Example 9

Injection Moulding Binder

The binder composition of Example 3 was injection moulded. The moulding conditions was as described in Example 8.

Figure 4:
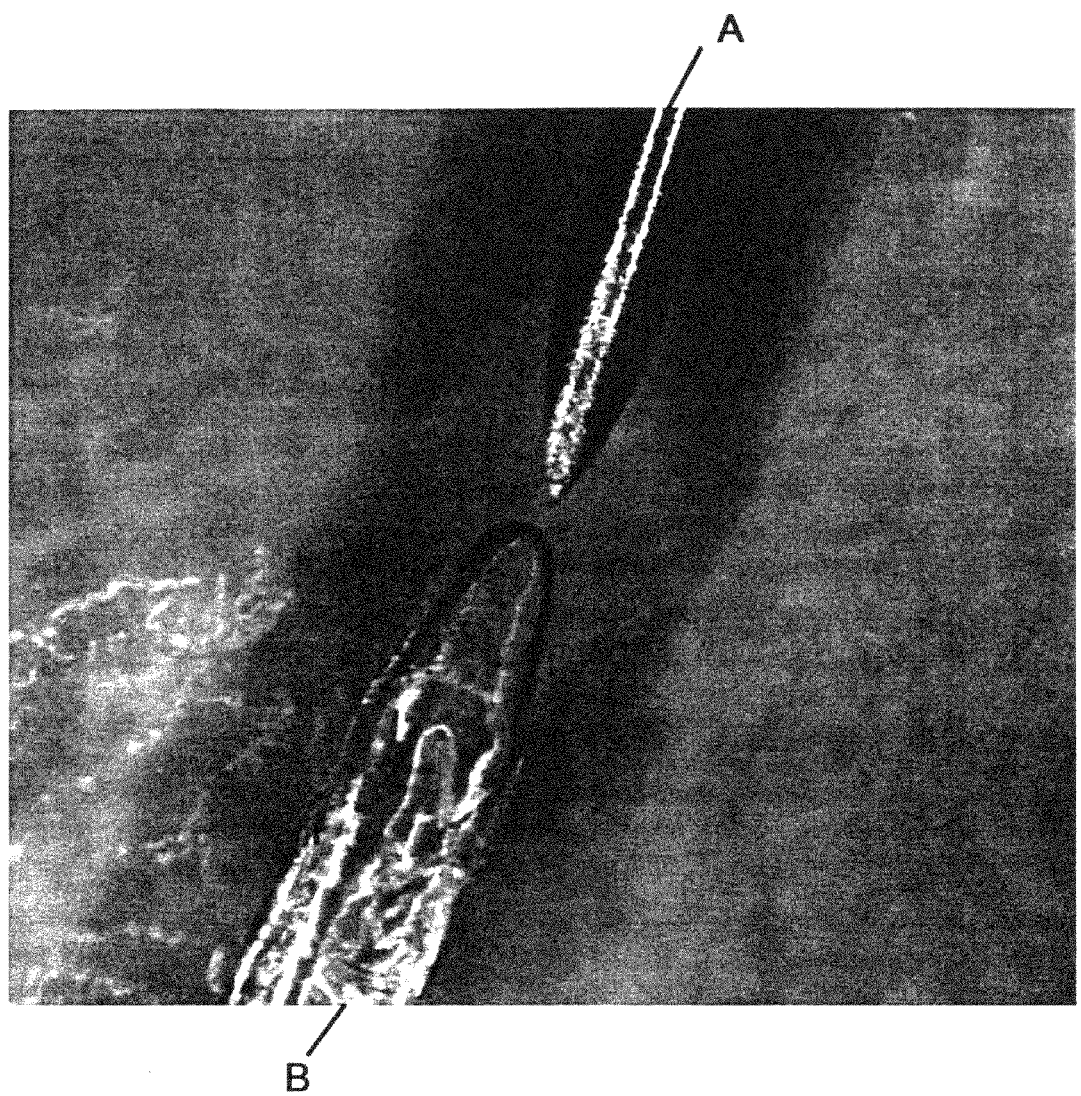
FIG. 4 is a photograph of a binder composition. A is a conventional cannula shown for comparison. B is an injection moulded binder composition (100% C*Maltidex H15323 (88% Maltitol) having a diameter of 0.5 mm.

The binder compositions obtained had a diameter of 0.5 mm and is shown in FIG. 4, wherein A is a conventional cannula shown for comparison and B is the composition.

The invention claimed is:
1. A method for preparing a solid pharmaceutical composition for parenteral injection comprising:
homogeneously mixing at least one therapeutic agent that constitutes at least 40% of the composition by weight with a binder that comprises at least one carbohydrate binding agent and constitutes at least 0.5% of the composition by weight, and,
at least one non-crystallization agent, so as to obtain an amorphous melt matrix,
shaping the melt matrix to a needle-shaped geometry using a mold cavity such that the solid pharmaceutical composition is capable of penetrating the epidermis, cutis or mucosa of a patient by injection without the assistance of a hypodermic needle or trocar,
cooling the amorphous melt matrix of the pharmaceutical composition to below the Tg of the binder, and
removing the composition from the mold cavity,
thereby providing a solid pharmaceutical composition.
2. The method of claim 1, wherein the melt is injected into a mold cavity having a predetermined geometry.

3. The method of claim 1, wherein the method comprises applying heat to obtain an amorphous matrix prior to mixing the therapeutic agent and binder.

4. The method of claim 1, wherein, prior to melting, the binder is dissolved in a solvent and dried to a solid amorphous matrix, and, optionally, disintegrated into a powder.

5. The method of claim 1, wherein the binder and the at least one therapeutic agent are mixed homogeneously as powders and the mixture is melted to form the melt.

6. The method of claim 4, wherein the solvent is water.

7. The method of claim 1, wherein the water content of the composition is less than 20% by weight.

8. The method of claim 1, wherein the Tg of the binder is at least 30° C.

9. The method of claim 1, wherein the viscosity of the composition is less than 50,000 Pa*s in a sub-range of the temperature interval between 60° C. and 140° C.

10. The method of claim 1, wherein the method is performed under essentially aseptic conditions.

11. The method of claim 1, wherein the composition is molded as the second part in a two component molding machine.

12. The method of claim 11, wherein a cartridge constituting the mold cavity is molded as the first part in a two component molding machine.

13. The method of claim 1, wherein the at least one non-crystallization agent is selected from the group consisting of maltose, sucrose, lactose, cellobiose, trehalose, maltulose, iso-maltulose, maltitol, sorbitol, mannitol, glucose, fructose, raffinose, melezitose, dextran, mannose, sorbose, melibiose, sophrose, turanose, lactulose, stachyose.

14. The method of claim 1, wherein the at least one binder is selected from the group consisting of maltose, sucrose, lactose, cellobiose, trehalose, maltulose, iso-maltulose, maltitol, sorbitol, mannitol, glucose, fructose, raffinose, melezitose, dextran, mannose, sorbose, melibiose, sophrose, turanose, lactulose, stachyose.

15. The method of claim 1, wherein the non-crystallization agent is selected from the group consisting of sorbitol, hydrogenated oligosaccharides, and combinations thereof.

16. The method of claim 1, wherein the at least one carbohydrate binding agent comprises maltitol.

17. The method of claim 1, wherein the at least one therapeutic agent is a protein selected from the group of insulin, glucagon, growth hormone, growth factors, blood factors such as FVII or FVIII, GLP-1, EPO, TPO, and interferon.

* * * * *